United States Patent
Shultz et al.

(10) Patent No.: US 10,261,076 B2
(45) Date of Patent: Apr. 16, 2019

(54) METHOD FOR DETECTING SMALL MOLECULE ANALYTES USING MAGNETORESISTANT SENSORS

(71) Applicant: The Board of Trustees of the Leland Stanford Junior University, Palo Alto, CA (US)

(72) Inventors: Tyler O'Brien Shultz, Los Gatos, CA (US); Jung-Rok Lee, Menlo Park, CA (US); Shan X. Wang, Portola Valley, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 26 days.

(21) Appl. No.: 15/281,793

(22) Filed: Sep. 30, 2016

(65) Prior Publication Data
US 2017/0097337 A1 Apr. 6, 2017

Related U.S. Application Data

(60) Provisional application No. 62/236,708, filed on Oct. 2, 2015.

(51) Int. Cl.
*G01N 33/543* (2006.01)

(52) U.S. Cl.
CPC .............. *G01N 33/54373* (2013.01)

(58) Field of Classification Search
CPC ..... G01N 33/54373; G11B 5/127; C12Q 1/68
See application file for complete search history.

(56) References Cited

U.S. PATENT DOCUMENTS

| 7,785,819 B2 | 8/2010 | Robinson |
| 7,906,345 B2 | 3/2011 | Wang |
| 8,318,093 B2 | 11/2012 | Wang |
| 2009/0117670 A1* | 5/2009 | Van Der Wijk ..... G01N 27/745 436/526 |
| 2010/0267169 A1* | 10/2010 | Hajimiri ............ G01N 27/3278 436/518 |

(Continued)

OTHER PUBLICATIONS

Li, Yuanpeng. (2015). Magnetic Biosensing System. Retrieved from the University of Minnesota Digital Conservancy, http://hdl.handle.net/11299/174868, publicly available May 2015 (Year: 2015).*

(Continued)

*Primary Examiner* — Narayan K Bhat
(74) *Attorney, Agent, or Firm* — Lumen Patent Firm

(57) ABSTRACT

Small molecule analytes (less than 1000 Daltons) in a fluid sample are detected using a competitive assay in a magnetic biosensor. The fluid sample is added to a biosensor detection chamber together with detection probes and magnetic tags which bind to the detection probes. The magnetic biosensor is functionalized with a capture probe that shares an epitope with the analytes, and the detection probe is capable of binding the epitope shared by the analytes and the capture probe, so that the presence of the analyte prevents detection probes (and magnetic tags) from binding to the biosensor. By measuring the binding of the magnetic tags to the magnetic biosensor, an amount of analytes in the solution is determined.

18 Claims, 18 Drawing Sheets

(56) References Cited

U.S. PATENT DOCUMENTS

2011/0014719 A1* 1/2011 Sijbers .................... B03C 1/282
436/150
2013/0102489 A1* 4/2013 Osterfeld ............. G01N 33/587
506/9

OTHER PUBLICATIONS

Li, Yuanpeng. (2015). Magnetic Biosensing System. Retrieved from the University of Minnesota Digital Conservancy, http://hdl.handle.net/11299/174868, publicly available May 2015—date support document (Year: 2015).*

Lee et al., "Small Molecule Detection in Saliva Facilitates Portable Tests of Marijuana Abuse," Anal. Chem. 2016, 88, 7457-7461.

Hun et al., "Aptamer biosensor for highly sensitive and selective detection of dopamine using ubiquitous personal glucose meters," Sensors and Actuators B 209 (2015) 596-601.

* cited by examiner

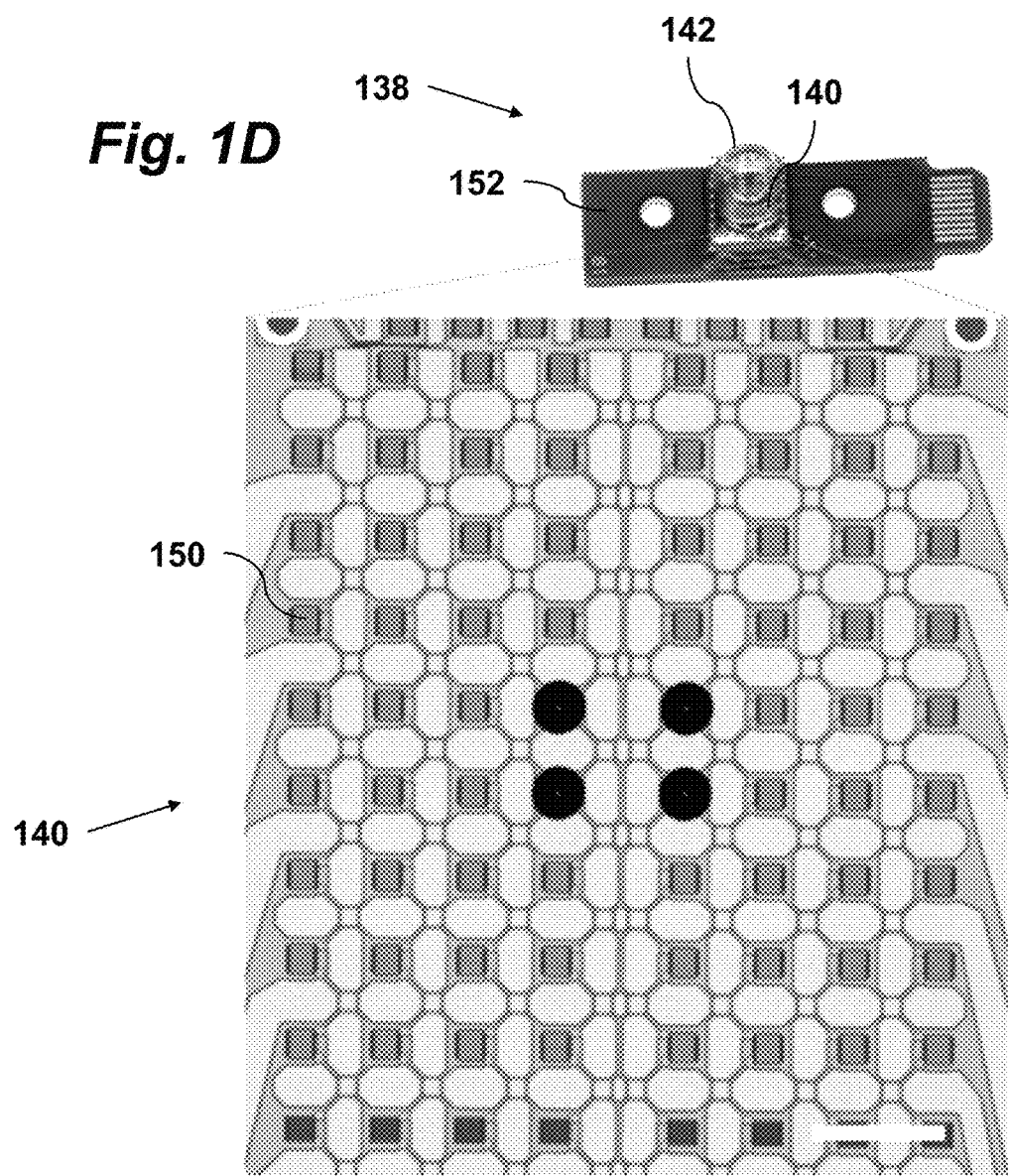

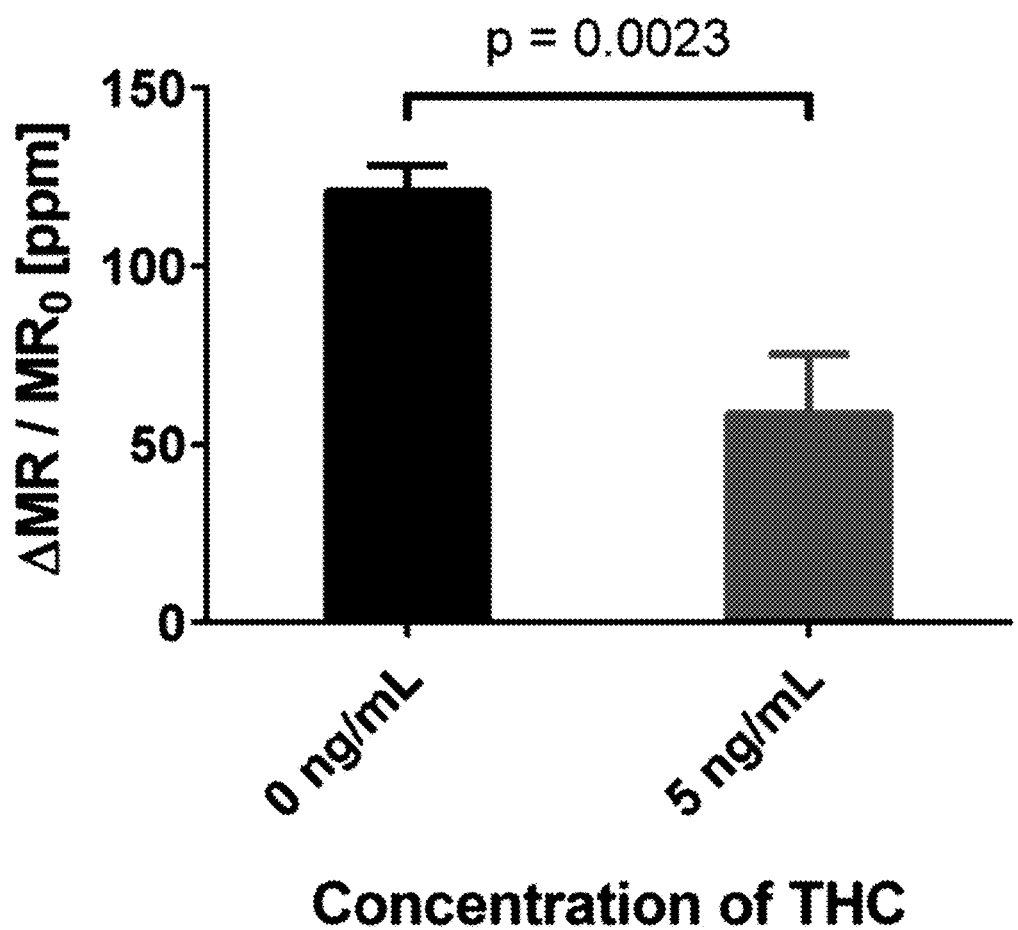

METHOD FOR DETECTING SMALL MOLECULE ANALYTES USING MAGNETORESISTANT SENSORS

CROSS-REFERENCE TO RELATED APPLICATIONS

This application claims priority from U.S. Provisional Patent Application 62/236,708 filed Oct. 2, 2015, which is incorporated herein by reference.

FIELD OF THE INVENTION

The invention relates generally to biosensing devices and techniques. More specifically, it relates to methods of detecting small molecule analytes in samples using magnetic sensors.

BACKGROUND OF THE INVENTION

The need for methods to detect small molecule analytes in small quantities has motivated the development of a variety of biosensing techniques. For example, current high sensitivity immunoassay techniques use a competitive assay reaction scheme that requires washing between sample addition and analyte detection to remove background signal and provide required sensitivity. This washing adds additional steps and complexity to the technique, limiting its use. There remains a need for biosensing techniques with very high sensitivity that are simple enough to be suitable for point of care applications.

SUMMARY OF THE INVENTION

In one aspect, the present invention provides a technique for detection of small molecule analytes without sacrificing sensitivity. To the best of our knowledge, this is the first demonstration of magnetic biosensors that are capable of detecting small molecules (i.e., molecules less than 1000 Daltons in molecular weight). A method for detecting small molecule analytes according to embodiments of the invention uses magnetic sensors and nanoparticle tags. The assay involves a capture probe, which shares an epitope with the sample analyte. The capture probe competes with the sample analyte for small molecule detection probes (such as antibodies, Fab fragments, single chain variable fragments, aptamers, or whole receptors). This capture probe is immobilized onto the surface of a sensor to capture detection probes in close proximity to the sensor. The presence of the analyte of interest in the sample interferes with the binding of the detection probes to the capture probes in a concentration dependent manner. After the detection probe binds the capture probe, the binding of magnetic tag to the detection probe brings the magnetic tag into close proximity to the sensor, which then detects the binding event. The binding of detection probes to the capture probe inversely relates to the degree to which the detection probe has been bound by sample analyte in solution. Thus, the amount of sample analyte in solution can be calculated.

In one aspect of the invention, a method is provided for detection of analytes in a fluid sample using competitive assay in a magnetic biosensor. The method includes adding the fluid sample containing the analytes, detection probes, and magnetic tags to the magnetic biosensor. The analytes being detected are small molecules, which is defined herein to mean that they have weights less than 1000 Daltons. The magnetic biosensor is functionalized with a capture probe that shares an epitope with the analytes, and the detection probe is capable of binding the epitope shared by the analytes and the capture probe. The method also includes measuring binding of the magnetic tags to the magnetic biosensor via the detection probes and the capture probes, and determining an amount of analytes in the solution from the measured binding of the magnetic tags to the magnetic biosensor.

In some instances of the method, two or more of the fluid sample, detection probes, and magnetic tags may be mixed together prior to adding them to the magnetic biosensor. For example, the detection probes and the magnetic tags may be conjugated prior to their addition to the magnetic biosensor. In other instances of the method, the fluid sample, detection probes, and magnetic tags may be added to the magnetic biosensor sequentially. In the present context, adding a compound to the biosensor is understood to mean introducing it to a biosensor reaction chamber containing a biosensor element so that it can react with the biosensor element.

The magnetic biosensor preferably includes multiple magnetic biosensor elements. Some implementations include control biosensor elements that are not functionalized with capture probes that can bind to the analytes or to the detection molecules, in which case determining the amount of the analytes includes comparing the measurements of binding of the magnetic tags to the magnetic biosensor with measurements from the control biosensor elements. In some implementations, the magnetic biosensor elements are functionalized with different types of capture probes that share corresponding distinct types of epitopes with multiple corresponding distinct types of analytes, and the fluid sample contains the multiple distinct types of analytes; the method then includes adding to the magnetic biosensor multiple distinct types of detection probes that are capable of binding the multiple corresponding distinct types of epitopes. The method may also include measuring binding of the magnetic tags to the magnetic biosensor elements functionalized with different types of capture probes, and determining amounts of the distinct types of analytes in the solution from the measured binding of the magnetic tags to the magnetic biosensor elements.

The amount of analytes in the solution may be determined from the measured binding of the magnetic tags to the magnetic biosensor by measuring electrical signals from magnetic biosensor elements (e.g., giant magnetoresistive sensors) to detect changes in electromagnetic properties of the biosensor elements due to binding of the magnetic tags.

In another aspect, the invention provides a method for detection of analytes in a fluid sample using direct binding in a magnetic biosensor. The method includes adding the fluid sample containing the analytes and magnetic tags to the magnetic biosensor. The analytes are small molecules that have weights less than 1000 Daltons. The magnetic biosensor is functionalized with a capture probe that changes conformation upon binding to the analytes, and the conformation changes enable the capture probe to bind to the magnetic tags. The method also includes measuring binding of the magnetic tags bound to the capture probes of the magnetic biosensor, and determining an amount of analytes in the solution from the measured binding of the magnetic tags to the capture probes.

BRIEF DESCRIPTION OF THE DRAWINGS

FIG. 1D shows detail of a disposable biosensor cartridge and a magnetic biosensor array contained in the cartridge, according to the embodiment of the invention shown in FIG. 1C.

FIG. 4B is a graph of GMR biosensor signal vs analyte concentration, according to an embodiment of the invention.

DETAILED DESCRIPTION

Figure 1A:
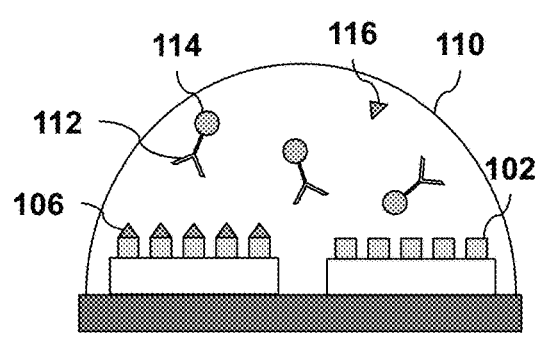
FIGS. 1A-B illustrate a biosensing technique using functionalized magnetic biosensors, and detector probes bound to magnetic tags, according to an embodiment of the invention.
Figure 1A:
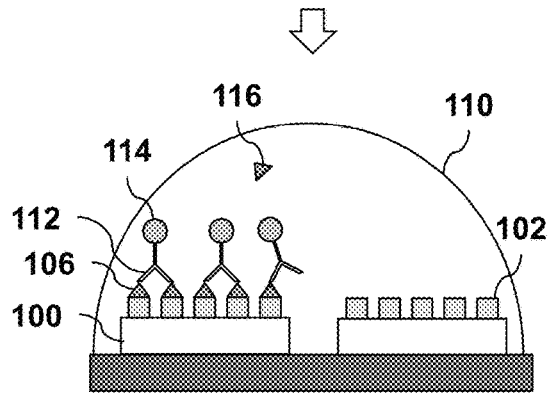
Figure 1B:
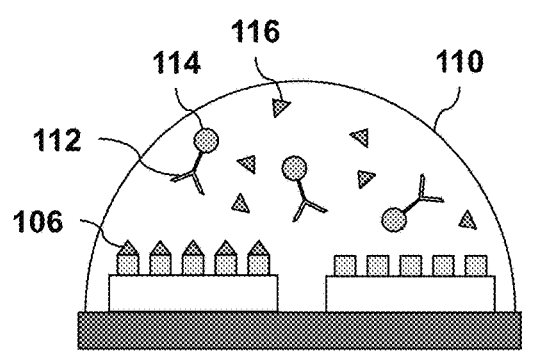
Figure 1B:
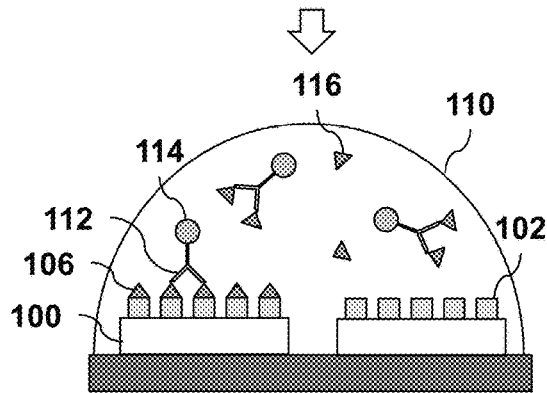

A biosensing technique according to one embodiment of the invention is illustrated in FIGS. 1A-B. Magnetic biosensor elements 100 are positioned on a substrate 104 and their surfaces are functionalized with capture probes 106. The biosensor elements are contained in a reaction chamber 110. Detection probes 112 that bind to magnetic tags 114, and a sample containing a small molecule analyte 116 are added to the chamber 110. The detection probes 112 are selected to be capable of binding to both the capture probe 106 and to the analyte 116. As a result, a lower concentration of the analyte results in more detection probes binding to the capture probes on the biosensor elements, as shown in FIG. 1A. This yields high signal output from the magnetic sensor element 100, whose signal depends on the magnetic tags 114 in close proximity to the surface of the element. Conversely, a higher concentration of analytes results in fewer detection probes binding to the capture probes on the biosensor elements due to significant competitive inhibition of the detection probe by the sample analyte, as shown in FIG. 1B. This yields lower signal output from the magnetic sensor element. There is thus an inverse relationship between the amount of analyte in sample to the signal output by a magnetic sensor in the competitive reaction scheme. In some embodiments, a biosensor element 102 is not functionalized to bind to the detection probe (i.e., either not functionalized at all, or functionalized such that it does not bind to the detection probe). The signal from element 102 can serve as a negative control sensor. In addition, or alternatively, elements may be functionalized to serve as positive control sensors. For example, the positive control sensors may be functionalized with capture probes that can directly bind to magnetic tags without binding to the analyte or detection probes, so that these sensors produce high signals.

Following the principles above, a method of detecting at least one analyte according to an embodiment of the invention uses the following competitive assay scheme:

1) Fabricate an array of magnetic sensors and functionalize the surfaces such that a capture probe can be bound to the sensor surface.

2) Spot the capture probe that shares an epitope with the analyte of interest.

3) Add sample containing the analyte of interest.

4) Add detection probe capable of binding the epitope shared by the analyte of interest and capture probe.

5) Add magnetic tags.

6) Monitor the binding of the magnetic tags to the detection probe bound to the capture probe, and determine the amount of sample analyte in the solution.

As an example of the technique adapted for detecting tetrahydrocannabinol (THC) analytes (314 Daltons) in a saliva sample, the biosensor elements may be giant manetoresistive (GMR) sensor elements functionalized with bovine serum albumin (BSA) conjugated with THC molecules. The detection probe is anti-THC bound to a magnetic nanoparticle complex. Other sensor elements may be functionalized with BSA or BSA-Biotin, which serve as biological negative and positive controls, respectively. The technique may be implemented using a system including an 10×8 array of giant magnetoresistive sensors. Saliva samples containing unknown amounts of THC are mixed with biotin labeled antibodies for THC and are added to the reaction chamber with the sensors. Binding of anti-THC antibodies to the BSA-THC coated sensors is monitored with the addition of streptavidin labeled magnetic nanoparticles. The amount of binding is concentration dependent and inversely related to the amount of THC in saliva. As more THC is added to the saliva sample, the signal from the GMR sensor decreases.

The technique may be implemented as a hand-held point-of-care device that enables rapid and precise detection of small amounts of THC without the need for washing. Until now, GMR biosensors have only been used to measure large proteins, with a focus on cancer diagnosis. The combination of GMR biosensor technology with a competitive immuno-assay assay scheme provides surprising improvement in biosensor sensitivity, with the ability to detect low nanomolar concentrations of very small molecules.

For illustrative purposes, an example of such a device for implementing the techniques of the present invention are now described in detail.

Figure 1C:
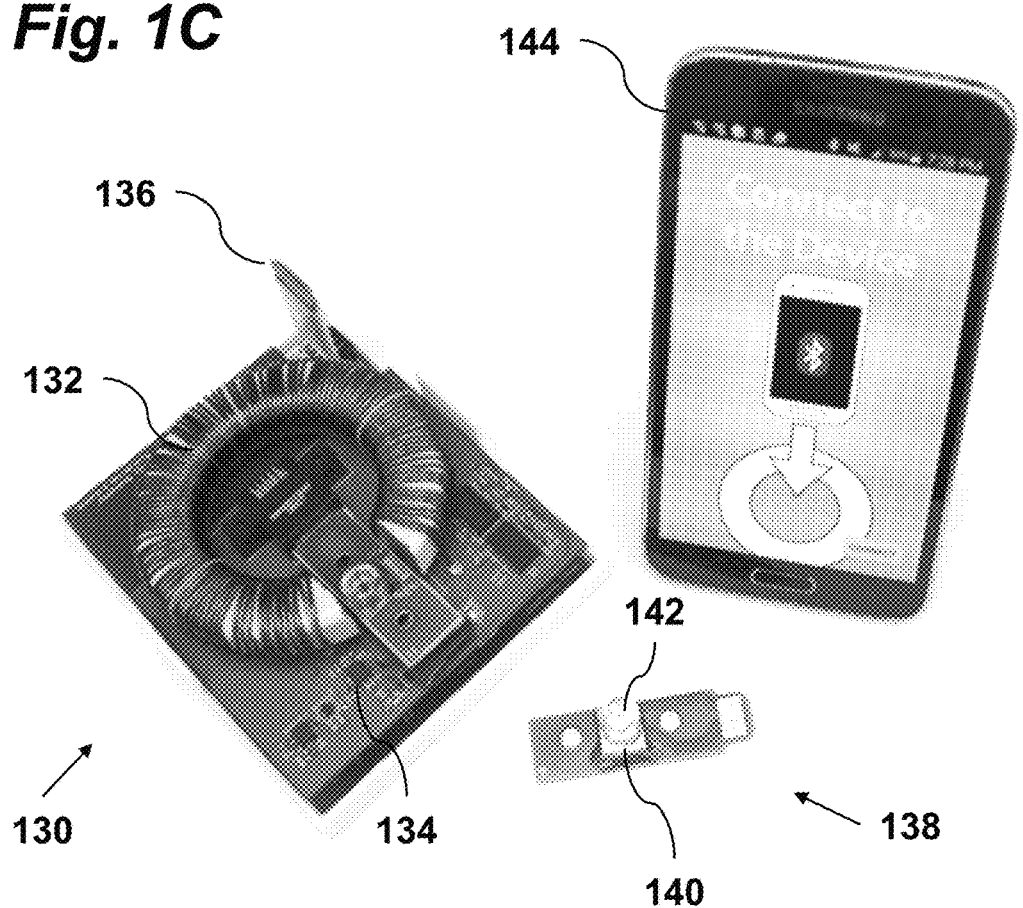
FIG. 1C shows a portable system for implementing a biosensing technique according to an embodiment of the invention.

FIG. 1C shows a mobile technology system that facilitates rapid and precise measurement of low nanomolar concentrations of THC in a 50 µl saliva sample in a 10 to 15 minute timeframe. It includes a giant magnetoresistive (GMR) reader 130 with a toroid core coil 132, electrical circuits 134, and Bluetooth module 136. The system also includes a disposable cartridge 138 is based on a customized design of printed circuit board (PCB) integrated with a GMR biosensor chip 140 and reaction chamber 142. A smartphone 144 with customized app wirelessly communicates with the reader 130 to control it, receive data, process the data from the biosensors, and display the results.

The disposable cartridge 138 and magnified view of the GMR biosensor chip 140 are shown in detail in FIG. 1D. The GMR biosensor chip 140 may be wire-bonded to a customized PCB 152, and the reaction chamber 142 may be glued on top of the chip. The to chip 140 has 80 sensors arranged in a 10 row by 8 column array. Each sensor, such as sensor element 150, can be individually functionalized for multiplex assays. The last (bottom) row of the array may be used as electrical reference sensors. As an example, capture probes (BSA or THC-BSA) were spotted on four sensors in the middle. The scale bar is 500 µm.

The array of GMR biosensors may be fabricated on a 10×12 mm piece of silicon wafer. An individual GMR biosensor has a spin valve structure of IrMn (8)/CoFe (2)/Ru (0.8)/CoFe (2)/Cu (2.3)/CoFe (4.5) (all thicknesses in nm) on seed layer, and has an active sensing area of 100×100 µm. Electrical pads are connected to the biosensors via a network grid type of electrodes to allow external access to individual biosensors. 30 nm and 300 nm of oxide layers are deposited on the active sensing area and the rest of the chip, respectively, to passivate the electrodes. After washed with acetone, methanol, and isopropanol, the chip is glued on a customized PCB, and wire-bonded to the electrical pads. Then, the chip is treated with 10% (3-Aminopropyl)triethoxysilane (APTES, Sigma-Aldrich, USA) in acetone for 30 min. After washing with acetone and distilled water sequentially, a reaction chamber is installed on top of the chip to accommodate samples and reagents. THC-BSA (Fitzgerald, USA), BSA (Sigma-Aldrich, USA), and biotinylated BSA (Sigma-Aldrich, USA) are then spotted on different sensors with replicates using a non-contact arrayer (Scienion, USA). The cartridge is stored overnight in a humid chamber at 4° C. The chip is washed with rinsing buffer (PBS pH 7.4 with 0.1% BSA and 0.05% Tween-20), and blocked with 1% BSA (Sigma-Aldrich, USA) for 1 hour before use.

Figure 1E:
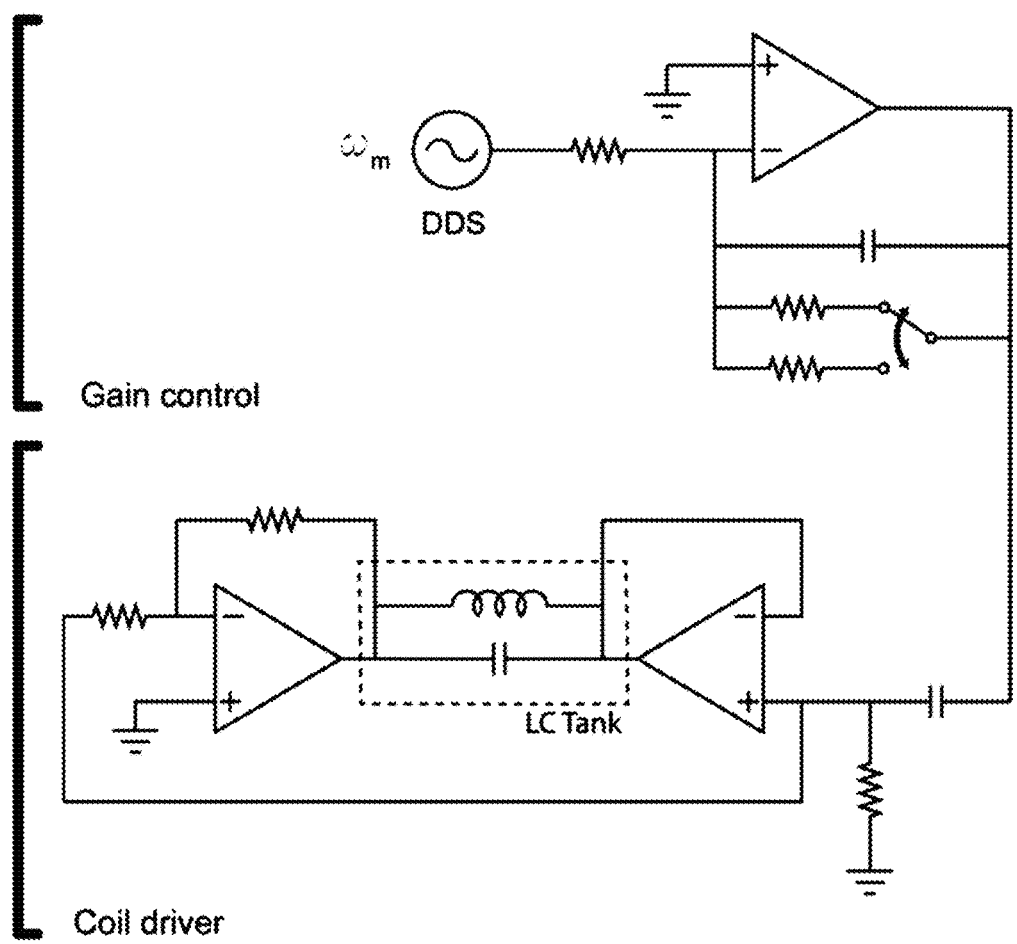
FIG. 1E is a schematic diagram of a coil driver circuit, according to the embodiment of the invention shown in FIG. 1C.

The measurement reader is composed of two stacked PCBs and a cartridge integrated with GMR biosensor chip. The two PCBs are connected via two connectors (16 pins and 20 pins). The top board is equipped with a receptacle for the cartridge and a toroid magnetic core coil with 470 g ceramic capacitor for LC resonance. The LC tank is driven by two power amplifiers in a bridge-tied load configuration on the top board as shown in FIG. 1E. A coil driver circuit includes a gain controlling unit and coil driving unit. The gain controlling unit produces two different magnitudes of magnetic field at the frequency of w to operate the reader and calibrate the sensor response. The coil driving unit operates a LC tank that incorporates a coil and ceramic capacitor using power amplifiers. Sinusoid signals at the resonant frequency and control signals for the gain of the magnetic fields are transferred via the 16 pin connector, and the 20 pin connector links GMR biosensors on the cartridge to the bottom board. The bottom board has analog and digital circuits to process the signals from GMR biosensors and to control a Bluetooth module to communicate with a smartphone.

Figure 1F:
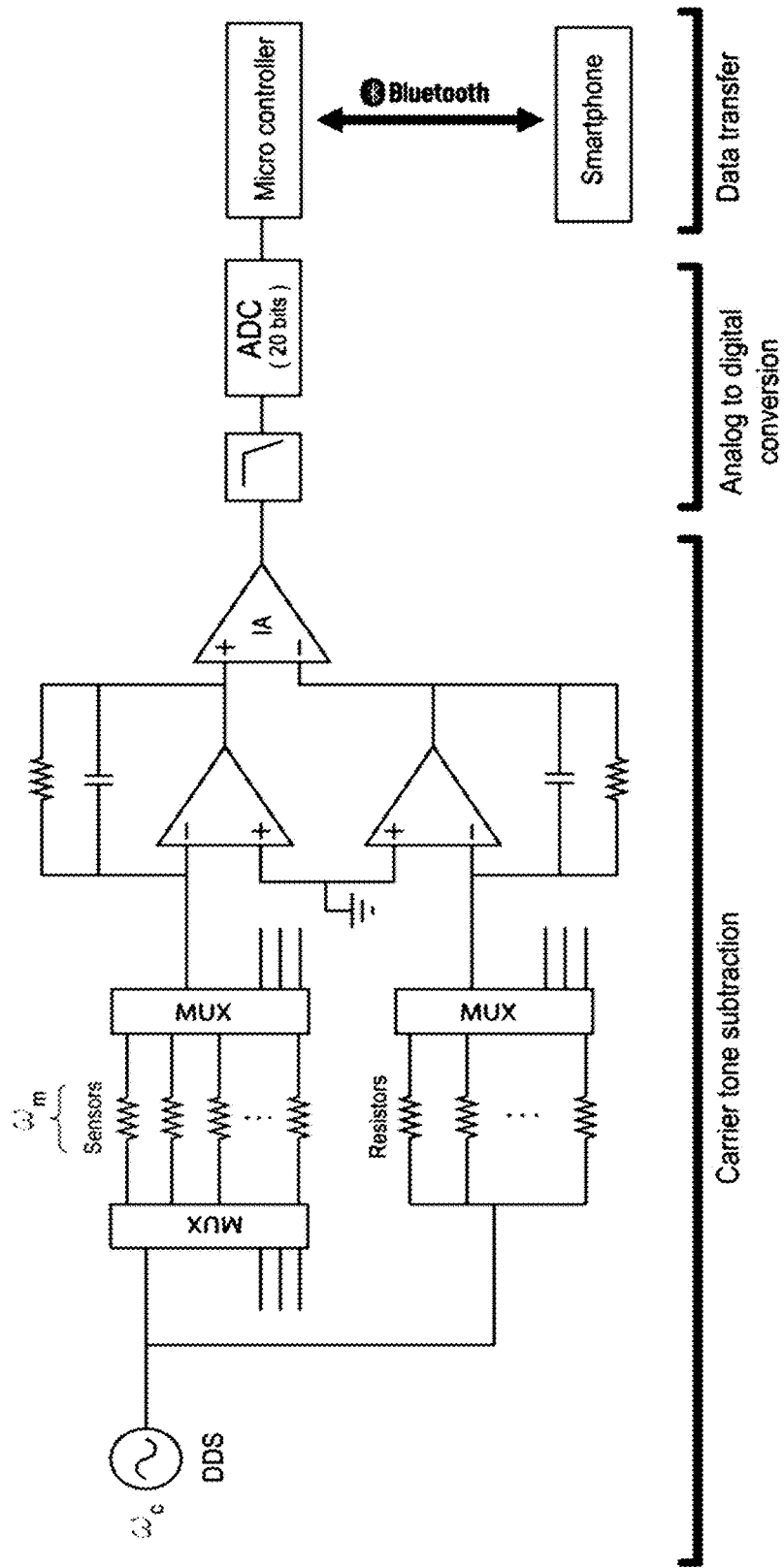
FIG. 1F is a magnetic biosensor array detection circuit, according to the embodiment of the invention shown in FIG. 1C.

To reduce the effect by flicker noise of GMR sensor, double modulation scheme is implemented as shown in FIG. 1F. Direct digital synthesizer (DDS) generates a carrier frequency ($\omega_c$) and a frequency for external magnetic field ($\omega_m$) to employ a double modulation scheme. A carrier tone subtraction circuit reduces the magnitude of the carrier tone by subtracting signals of pre-matched resistors from sensor signals. An analog to digital conversion (ADC) circuit converts amplified analog signals into 16-bit digital signals after the signals pass through an anti-aliasing filter. A micro-controller processes and transfers the data to a smartphone via Bluetooth.

The bottom PCB provides a sinusoidal voltage to the GMR sensors while the magnetic field generated by the toroid core coil magnetically excites the GMR biosensors. The electrical current from GMR biosensors is amplified by carrier tone subtraction circuit. Then the 20-bit ADC chip (Linear Technology, LTC2378) samples the amplified signal and transfers the digitized signal to the microcontroller (ATSAM3X8EAAU, Atmel Corporation) for further analysis with Fast Fourier Transform. Temperature and magnetoresistive ratio (MR) correction algorithm is used to remove changes in signal due to temperature fluctuation and variation in sensor fabrication. The microcontroller transferred the processed data to the Bluetooth module (HC-06) on the bottom board using Serial Peripheral Interface (SPI). Then, a smartphone connected via Bluetooth receives and displays the result on the screen using a custom app.

Figure 1G:
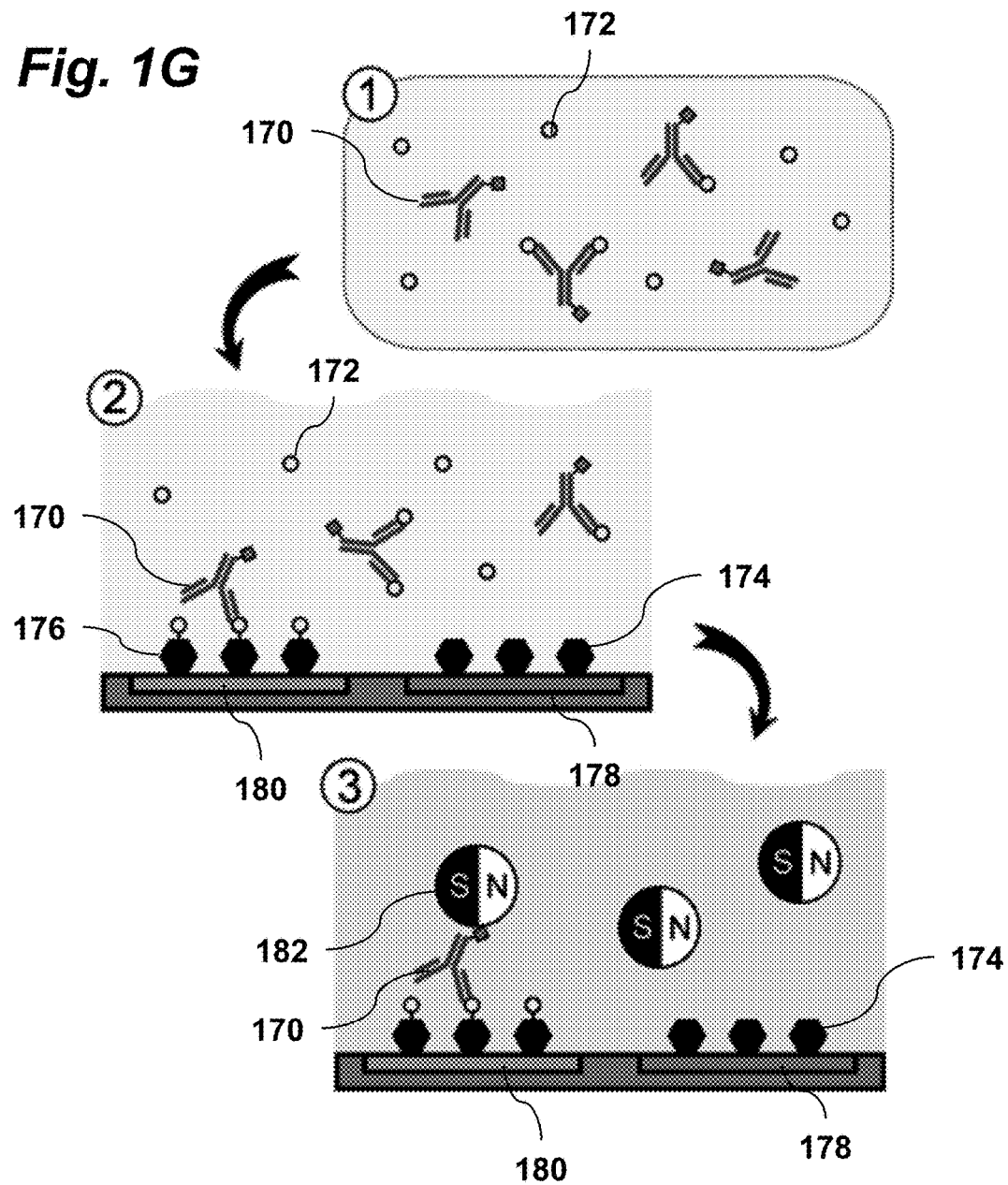
FIG. 1G is a schematic illustrating steps of a competitive assay used for magnetic biosensing of small analytes, according to an embodiment of the invention.

FIG. 1G is a schematic illustrating how the device is used to perform a competitive assay. Step 1: anti-THC biotinylated antibodies (detector probes) 170 are mixed with a sample containing THC molecules 172 and preincubated for 15 min to bind to THC.

Step 2: 50 µL of the mixture is added to the chip reaction chamber containing a functionalized biosensor chip. The chip has bovine serum albumin (BSA) 174 and THC-BSA 176 immobilized on different sensors 178, 180, respectively. In addition, some sensors are functionalized with biotinylated BSA (Biotin-BSA). The solution is incubated for unoccupied antibodies 170 to bind to THC-BSA 176 on the sensors for an additional 15 min.

Step 3: Unbound antibodies are washed, the disposable chip is inserted into the measurement reader, and 40 µL of streptavidin-coated MNPs 182 are then added to the chip reaction chamber, where they bind to antibodies 170. The stray field from the bound MNPs disturbs the magnetization of biosensors underneath, which changes the resistance of the biosensor. The changes in resistance, monitored as GMR biosensor signals ($\Delta MR/MR0$), are proportional to the number of bound MNPs and have an inverse relationship with the concentration of THC in the sample due to the nature of competitive assays.

After the cartridge is inserted into the measurement reader, a custom app based on the Android operating system (Google, USA) controls the measurement procedure. First, the app starts to measure the resistances of the biosensors to ensure whether the cartridge is inserted correctly and exclude defective biosensors of the chip from the measurement. By applying two different magnitudes of magnetic field to the sensors, the app calibrates the individual biosensors and normalizes the signals. Then, the app asks the user to add MNPs (Miltenyi Biotec, USA) to the chip and monitors signals from biotin-BSA-coated sensors. Signals from the THC-BSA, BSA, and biotinylated BSA (Biotin-BSA) sensors are monitored. The app automatically aborts the measurement if the biotin-BSA signals remain below 100 ppm until 1 min, which is a good indication that the user did not add the MNPs. Otherwise, the app continues to monitor all signals from different sensors up to 10 min. The raw data can be sent via email.

Figure 1H:
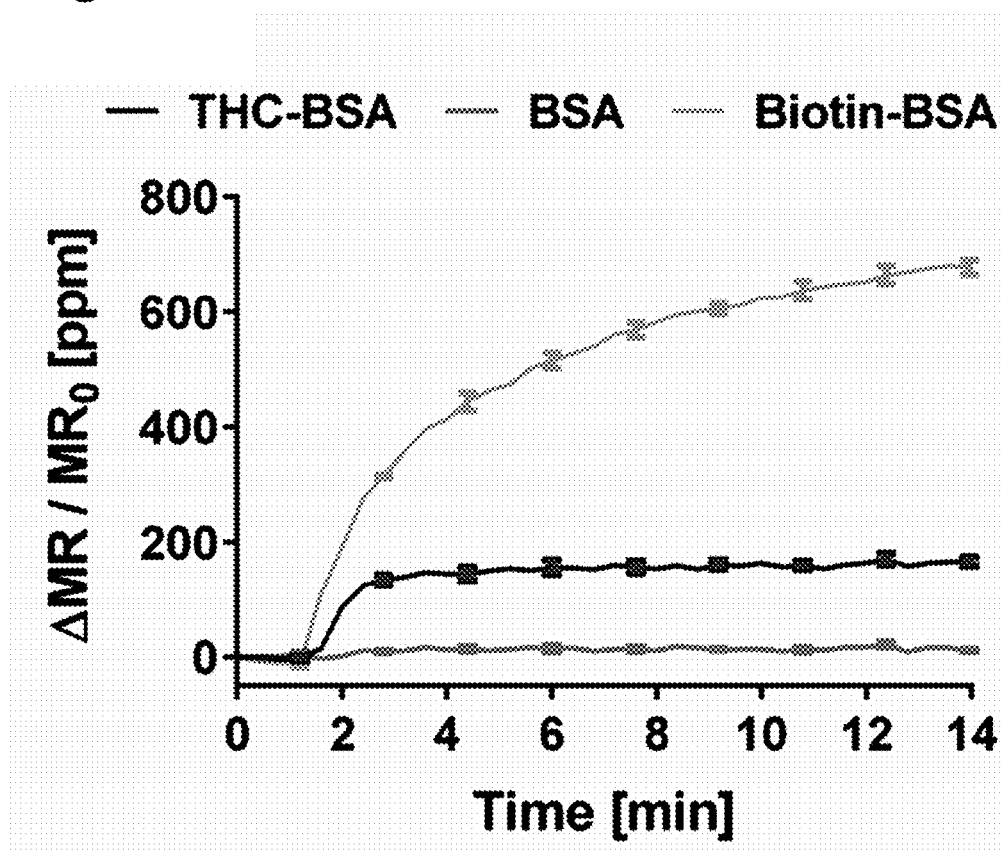
FIG. 1H is a graph of a real-time measurement of GMR biosensor signals for THC at 5 ng/mL in saliva, according to an embodiment of the invention.

FIG. 1H is a graph of a real-time measurement of GMR biosensor signals for THC at 5 ng/mL in saliva. The signals are the average of 8 identical sensor signals and referenced to the averaged signal from reference sensors. The error bars represent standard deviations of 8 identical sensor signals.

Figure 2:
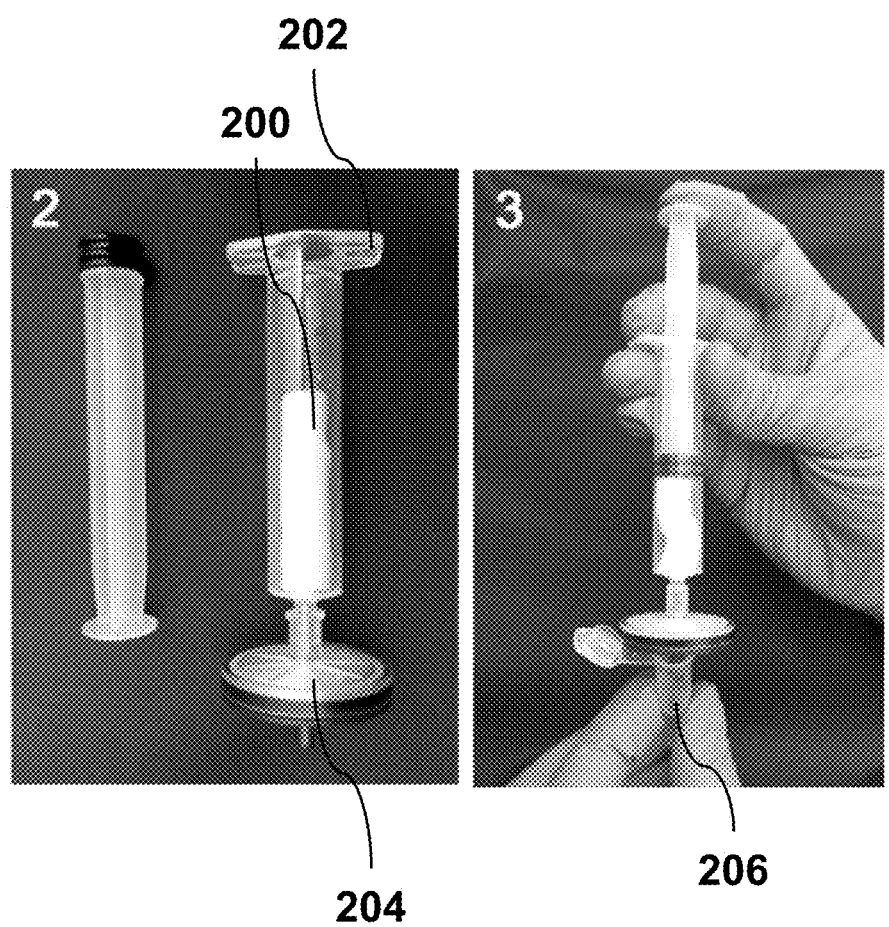
FIG. 2 illustrates how saliva samples can be easily collected using a cotton swab, syringe, and filter unit, according to an embodiment of the invention.

Saliva samples can be easily collected in the field using various techniques. For example, a simple sample collection strategy uses a cotton swab 200, syringe 202, and filter unit 204, as shown in FIG. 2. First, oral fluid is collected with a cotton swab. The cotton swab is placed for 1 or 2 min in the mouth of an individual who is being tested to fully absorb oral fluids. The filter unit is attached to the syringe, and the saturated cotton swab is inserted into the syringe. The plunger of the syringe is depressed to squeeze the cotton swab and release the fluid, forcing it out and through the filter unit attached to the syringe. The filter unit removes viscous mucus, food particles, and extra debris in the sample. The filtered fluid is then collected in a test tube 206.

Figure 3A:
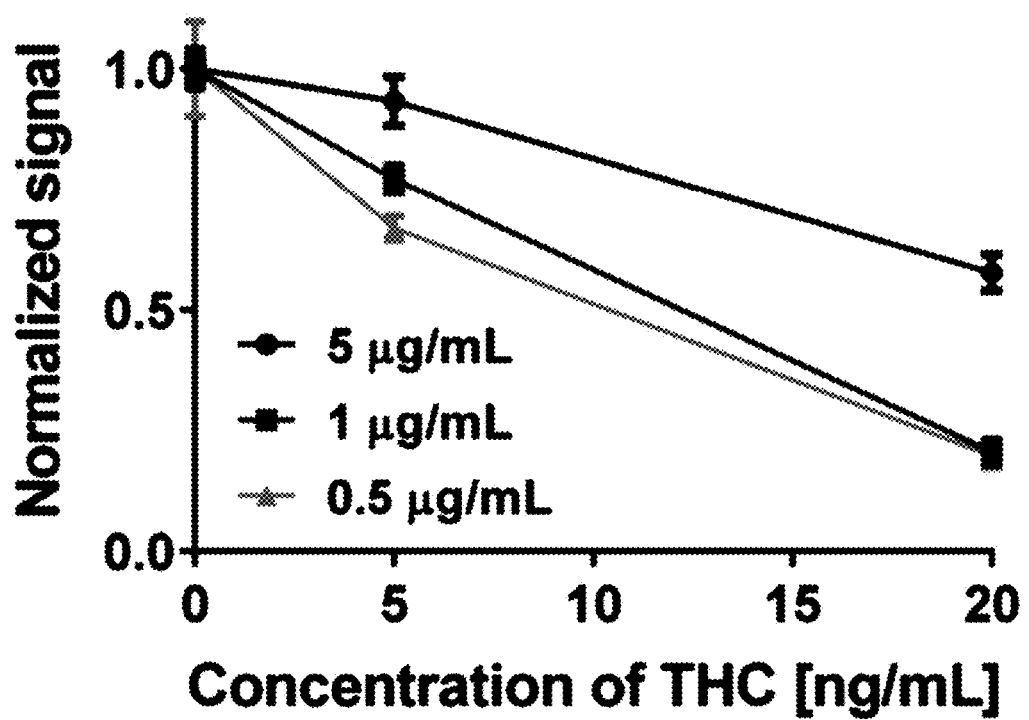
FIG. 3A is a graph of normalized measurement signal vs. concentration of analyte for three different concentrations of antibodies, according to an embodiment of the invention.

For THC detection, values ranging from 2 to 25 ng/mL are of interest. To achieve better sensitivity around this range, the preferred concentration of anti-THC biotinylated antibodies is 1 µg/mL. To arrive at this value, the inventors tested three different concentrations of antibodies (5, 1, and 0.5 µg/mL) with THC analyte concentrations at 0, 5 and 20 ng/mL, as shown in FIG. 3A. The signals at 5 and 20 ng/mL were normalized by the signal at 0 ng/mL for each antibody concentration for comparison. The antibodies at 5 µg/mL showed less reduction in signals as the concentration of THC increases compared to other antibody concentrations, which results in a wider dynamic range. The concentration of 1 µg/mL produced a fairly linear titration curve within the range, while 0.5 µg/mL showed a steeper drop at 5 ng/mL of THC but almost the same signal as 1 µg/mL of antibodies at 20 ng/mL of THC. In addition, the mass concentrations of antibodies (1 µg/mL) and THC (5 ng/mL) correspond to 7 nM and 16 nM in molar concentration, respectively. Considering the bivalency of the antibody, the binding capacity is well-matched. Thus, the depletion of antibodies by THC was effectively monitored in the competitive assays, and we therefore prefer antibodies at 1 µg/mL.

Figure 3B:
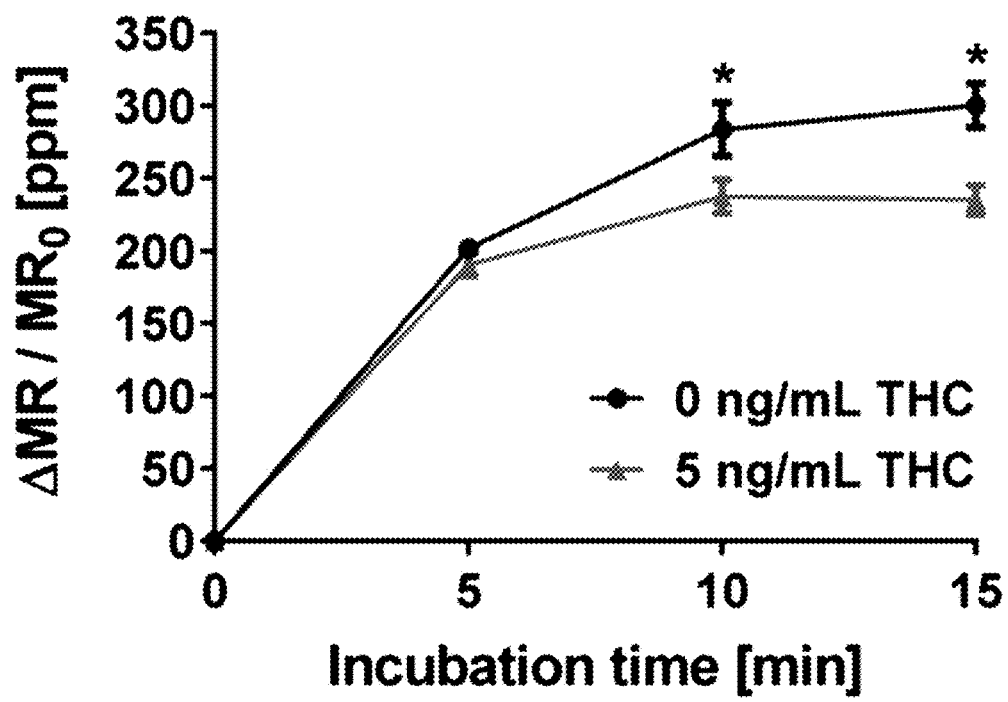
FIG. 3B is a graph of GMR biosensor signal vs sample incubation times for two different concentrations of analyte, according to an embodiment of the invention.
Figure 3C:
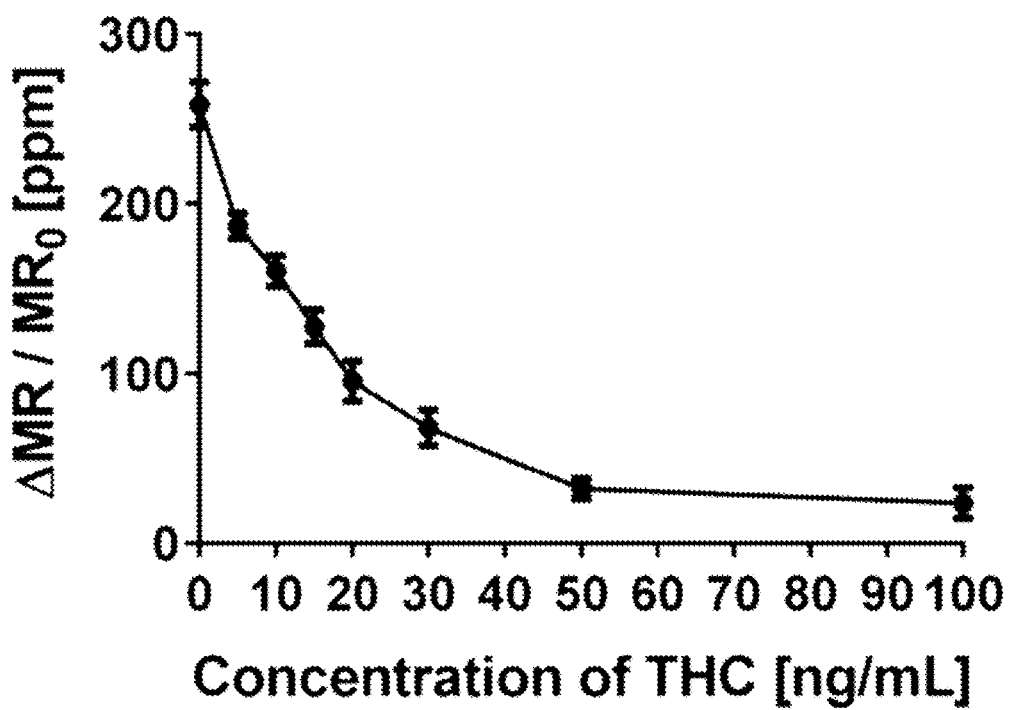
FIG. 3C is a graph of GMR biosensor signal vs analyte concentration, according to an embodiment of the invention.

To determine a preferred time frame for incubation of a sample mixture with the chip, three different incubation times (5, 10, and 15 min) for the chip incubation were tested with 15 min of preincubation (FIG. 3B). The antibodies at 1 µg/mL were used to detect both THC at 0 and 5 ng/mL with 3 different chip incubation durations. A 15 min preincubation was performed to mix the sample with antibodies. The data point is denoted with an asterisk if Welch's t-test shows p<0.01. The signals were saturated for around 15 min, and the difference between signals of 0 and 5 ng/mL of THC was maximized in the case of 15 min of chip incubation. Using these conditions (1 µg/mL of antibodies and 15 min/15 min incubation), we obtained a titration curve with a dynamic range from 0 to 50 ng/mL of THC in saliva (FIG. 3C). The concentration of THC in the sample varied from 0 to 100 ng/mL. The biotinylated antibodies at 1 µg/mL and 15 min preincubation/15 min chip incubation were used.

Figure 3D:
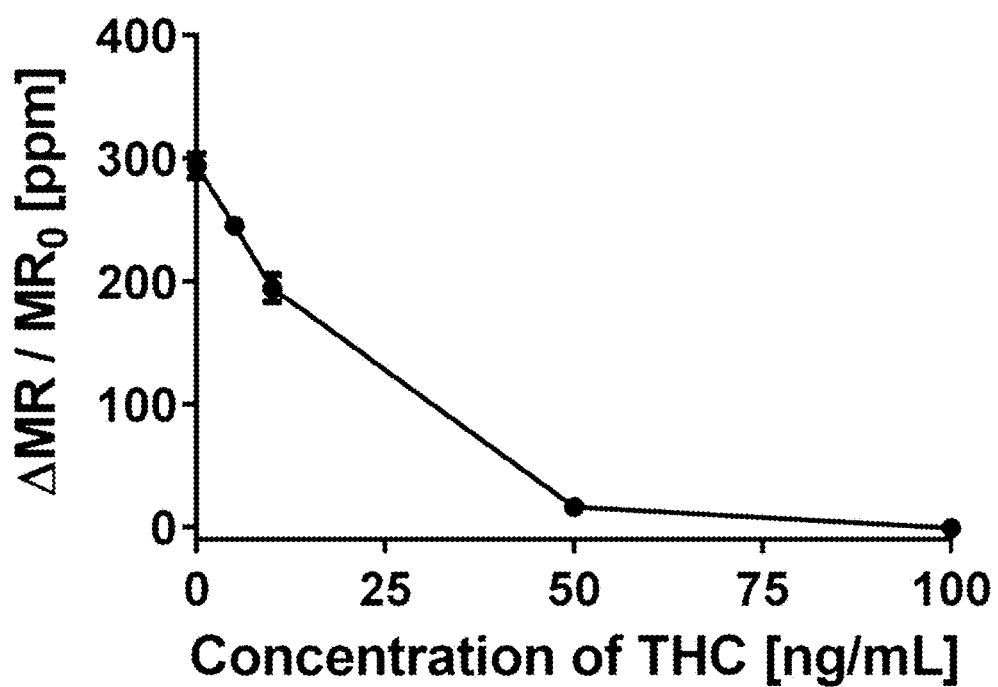
FIG. 3D is a graph of GMR biosensor signal vs analyte concentration, according to an embodiment of the invention.
Figure 3E:
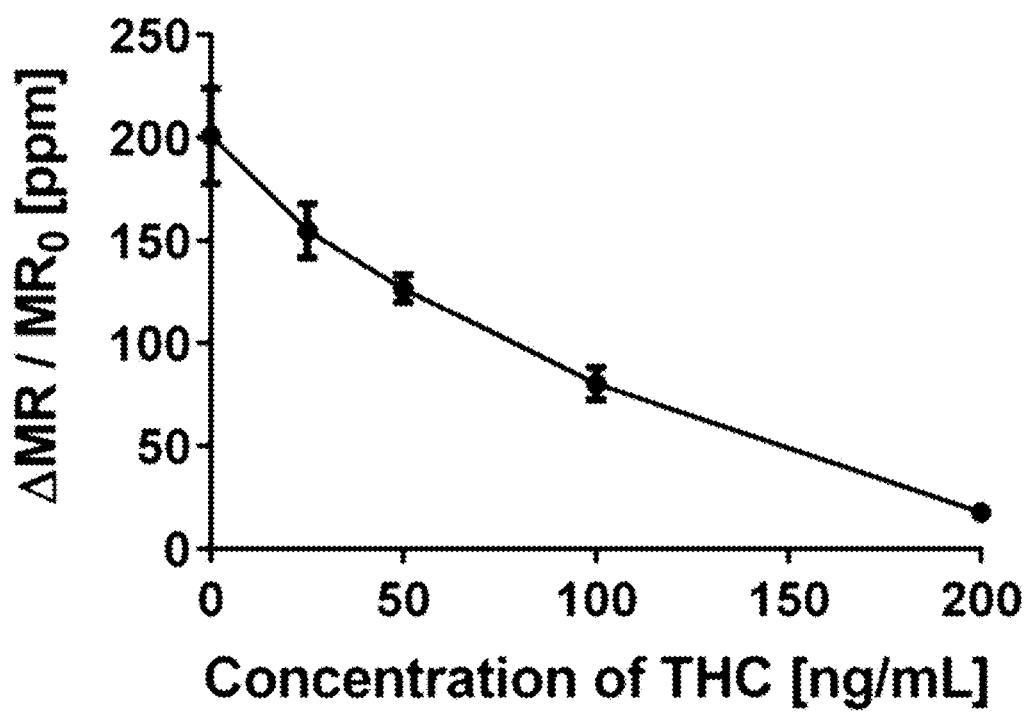
FIG. 3E is a graph of GMR biosensor signal vs analyte concentration, according to an embodiment of the invention.

Furthermore, preincubation and chip-incubation times were reduced to 5 and 10 min, respectively, and the GMR sensor signals were taken at 5 min after adding MNPs instead of 10 min to carry out the entire measurement within 20 min. FIG. 3D shows a titration curve of 20 min assays. The same concentration of anti-THC biotinylated antibodies (1 µg/mL) was used. 5 min of pre-incubation and 10 min of incubation with the chip were performed. The signals were obtained 5 min after adding MNPs. The result showed no significant loss in performance. This was because the signal levels of 10 min chip-incubation was fairly close to those of 15 min incubation as shown in FIG. 3B, and the sensor signals typically reached their plateaus within less than 5 min after addition of MNPs as shown in FIG. 1H. Moreover, the result revealed that preincubation time was still not a limiting factor when it was set to 5 min. Since the preincubation is three-dimensional mixing and binding between THC and antibodies, which is much faster than binding of antibodies to THC on planar surfaces during the chip-incubation, the preincubation could be further reduced, compared to the chip-incubation. Without any preincubation, THC in a wider dynamic range (0 to 200 ng/mL) was detected with 5 µg/mL of antibodies within 3 min of total assay time (FIG. 3E). The mixture of the sample and antibody was immediately added to the chip and incubated for 2 min. The concentration of the antibodies was 5 µg/mL, and the signals were obtained 1 min after adding MNPs. The signals are the average of 4 identical sensors, and the error bars represent the standard deviations. In this case, a higher concentration of antibodies warranted less chip-incubation time to obtain a substantial signal of antibody binding to THC on the surface. In a similar manner, the assay can be further tailored to adjust the sensitivity and dynamic range by changing antibody concentration and incubation time if the cutoff concentration of THC is beyond the current range.

The array of sensors may be split into two groups and compartmentalized with separate reaction chambers. One of the compartments is used to measure a sample with known concentrations of analytes or without any of them, and the other compartment is used to measure unknown sample or sample of interest. The difference in signals between the sensors with the same capture probe in different compartments can be used to determine the concentrations of analyes in the unknown sample or sample of interest.

Figure 4A:
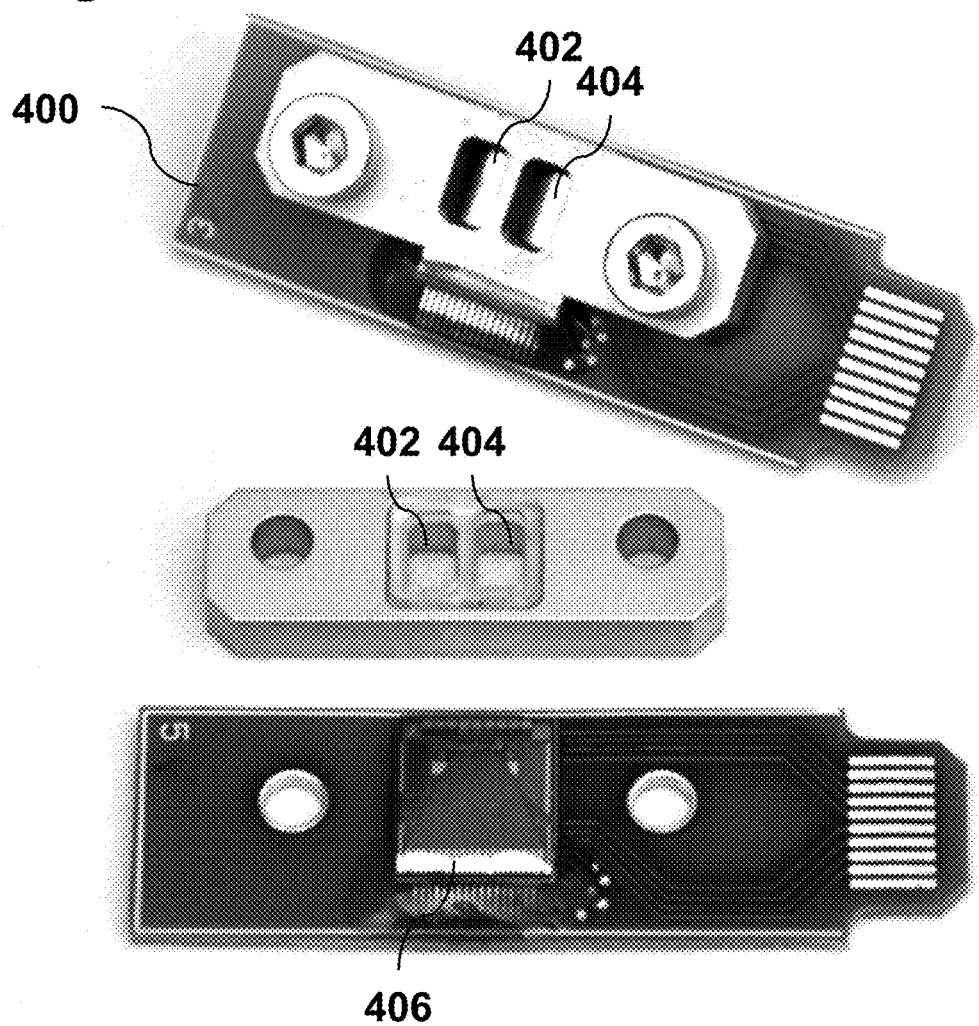
FIG. 4A illustrates assembled and disassembled views of a biosensor cartridge with two reaction chambers, according to an embodiment of the invention.

Since the binding of the antibodies to THC is a thermodynamic process, the temperature affects the assay results and there are day-to-day variations in measurement signals due to temperature fluctuations, chip-to-chip variations, or incubation time variations. Thus, to increase accuracy of the assay and minimize the measurement variation, a two-compartment cartridge 400 where two reaction chambers 402, 404 with a gasket made of polydimethylsiloxane (PDMS) are used with a GMR biosensor chip 406 to measure both the sample of interest and a reference sample simultaneously with the same chip 406 (FIG. 4A). The use of two compartments ensures that both samples experience the same experimental condition including temperature, incubation time, and biochip fabrication. Each compartment includes 20 biosensors. Since two samples are measured with the same chip at the same time, all measurement variation such as chip-to-chip variation, temperature fluctuation, and reagent variation can be reduced or even eliminated. For demonstration, saliva samples containing 0 and 5 ng/mL of THC, respectively, were measured with the two-compartment cartridge. With the measurement using the two-compartment cartridge, the tester can easily determine whether the test result is positive or negative by the difference between the signals of two samples. For example, if it is assumed that the cutoff concentration is 5 ng/mL (reference sample) and the sample without THC (0 ng/mL) is collected for testing, the test result is negative, i.e., a higher signal than the reference sample means negative, and a signal lower than or equal to the reference is positive. FIG. 4B is a graph of signals from 4 THC-BSA coated sensors in each compartment. The p-value was determined using Welch's t-test.

Figure 4C:
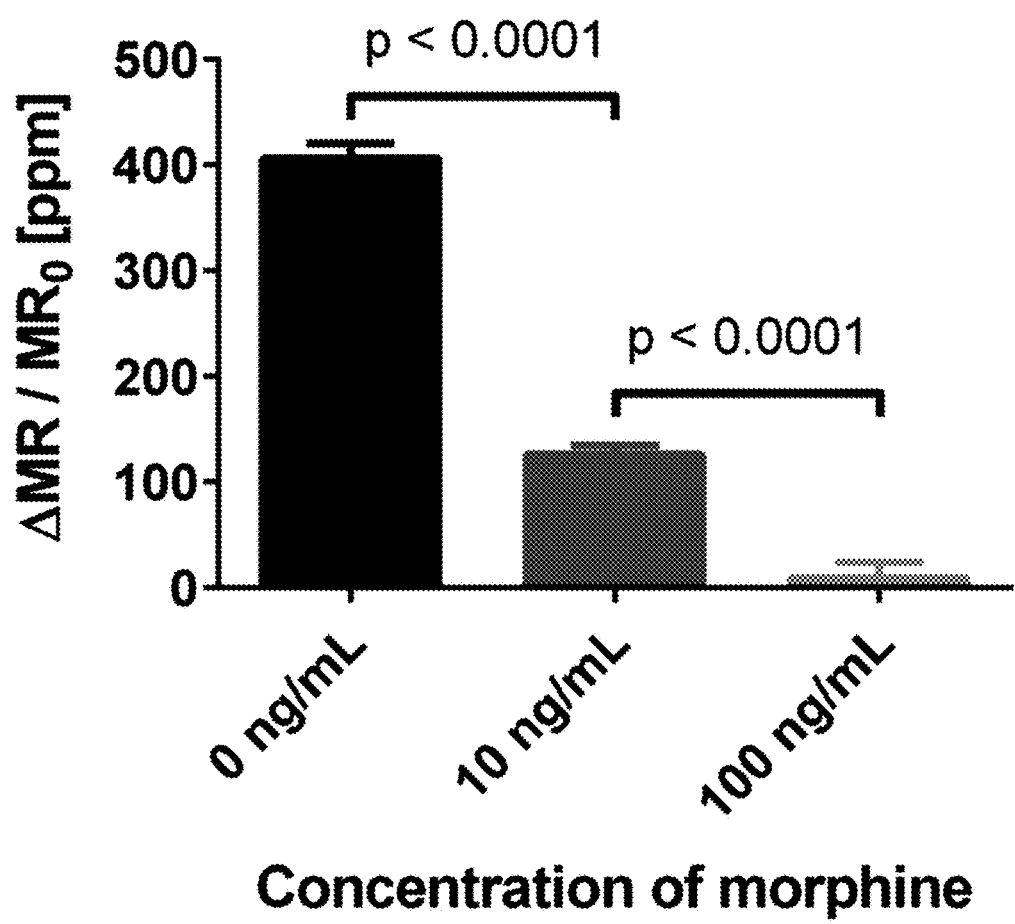
FIG. 4C is a graph of GMR biosensor signal vs analyte (morphine) concentration, according to an embodiment of the invention.

Although the examples discussed above for illustrative purposes focus on THC, the techniques of the present invention are not limited to THC, but are generally applicable to other small molecules. For example, the technique was demonstrated with morphine (285.3 Da) by replacing THC with morphine. The sensors were coated with morphine-BSA in lieu of THC-BSA, and antimorphine antibodies at 0.1 µg/mL were used. The signals from zero analyte, morphine at 10 and 100 ng/mL showed statistically significant differences. FIG. 4C shows the measurement of morphine spiked in saliva. 90 µL of saliva contains morphine (Cerilliant, USA) at the indicated concentration was mixed with 10 µL of biotinylated anti-morphine antibodies (Bioss, USA) for 15 min incubation. 50 µL of the mixture was added to the chip where morphine conjugated with BSA (morphine-BSA, Fitzgerald, USA) is immobilized on the sensors for 15 min incubation. After washing the chip, the chip was inserted into the reader. 40 µL of MNPs were added to the chip, and the signals were taken 15 min after addition of MNPs. The p-values were determined using Welch's t-tests.

Since the competitive assays are applicable to detection of any type of small molecules, the platform could be used to detect different drugs such as heroin and cocaine in addition to THC and morphine as well as to detect therapeutic small molecule inhibitors in cancer treatments.

In some embodiments of the invention, different capture probes for detecting different small molecules may be functionalized on different sensors in the array of sensors to perform multiplex assays. Then, the corresponding detection probes that can bind their target analytes specifically are added to the biosensor. For example, with the multiplexing capability of the GMR biosensor chip, the technique can be used to simultaneously detect multiple analytes (e.g., THC-COOH and THC, or THC and its metabolites in blood and urine).

Figure 5:
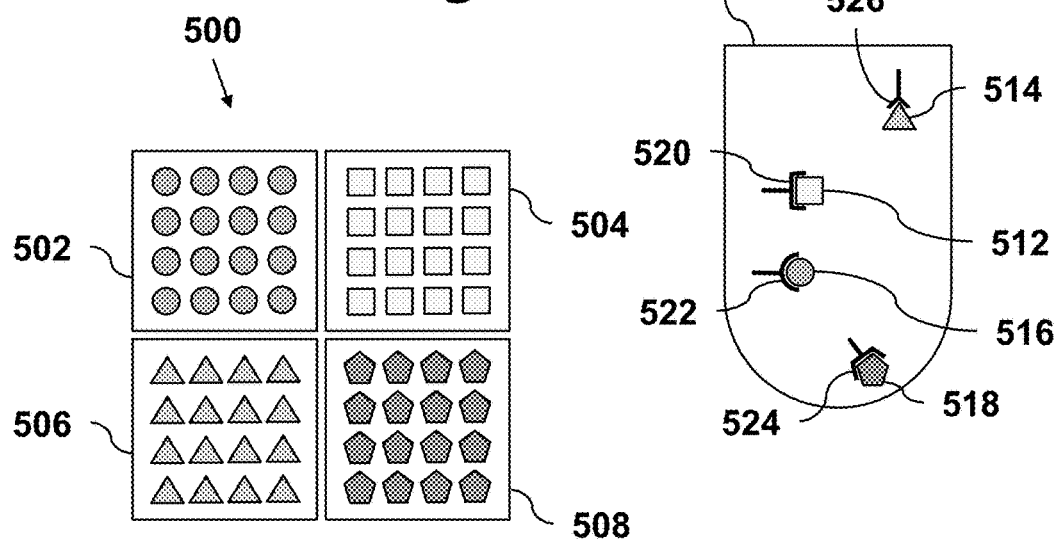
FIG. 5. is a schematic illustration of a multiplexing magnetic biosensor array and method for detecting multiple distinct types of small analytes, according to an embodiment of the invention.

An example of a multiplexing magnetic biosensor array 500 is shown in FIG. 5. It has multiple magnetic biosensor elements grouped in four regions 502, 504, 506, 508. The biosensor elements in each region are functionalized with a common type of capture probe that is different from the type of capture probe in the other regions. Each type of capture probe shares a corresponding distinct epitope with a corresponding distinct type of analyte. In effect, it is an implementation that performs the single-analyte method in parallel in a single sensor. A fluid sample 510 contains the multiple distinct types of analytes 512, 514, 516, 518. Multiple distinct types of detection probes 520, 522, 524, 526 that are capable of binding the multiple corresponding distinct types of epitopes are then added. The binding of the magnetic tags to the magnetic biosensor elements functionalized with different types of capture probes is measured, and the amounts of the distinct types of analytes in the solution is determined from the measured binding of the magnetic tags to the magnetic biosensor elements. This multiplexing technique can also be combined with the use of positive and negative control sensor regions, as described earlier.

It will be appreciated that the principles of the invention are not limited to the specific techniques or devices described above for illustrative purposes, but may be altered in various ways. For example, The reaction scheme may have variations, such as:

a) The detection probe and magnetic tags may be pre-conjugated, then added to the sensor array after addition of sample.

b) The detection probe and magnetic tags may be pre-conjugated, pre-mixed with sample, and then added to the sensor array as one whole mixture.

c) The detection probe, magnetic tags, and sample may be simultaneously pre-mixed prior to addition to the sensor array.

d) The detection probe, magnetic tags, or a conjugate of the two may be lyophilized on or in proximity to the array of sensors.

The reagents may be delivered via microfluidics. The reagents may be delivered via paper-based or gel-based platform to the sensor or via lateral flow method.

Mechanical stimulation such as shaking, vibrating, or stirring may be used to mix reagents.

The capture probe may be spotted on each sensor locally by surface tension of the solution, structural confinement, chemical treatment (e.g., hydrophobic/philic treatment), or delivery via an imprinting method.

The magnetic sensors may be magnetic tunnel junction sensors, Hall effect sensors, or magnetoresistive sensors such as anisotropic magnetoresistive sensors and giant magnetoresistive sensors.

The magnetic tags may be magnetic beads, magnetic nanoparticles, magnetic disks, and magnetic rods. They can bind to the detection probes via protein-protein interactions, DNA-DNA interaction, or chemical reactions.

An aptamer may be used instead of an antibody for the detection probe. In some cases, this could yield improved sensitivity, specificity, and provide a more thermally stable alternative to an antibody based approach.

Figure 4D:
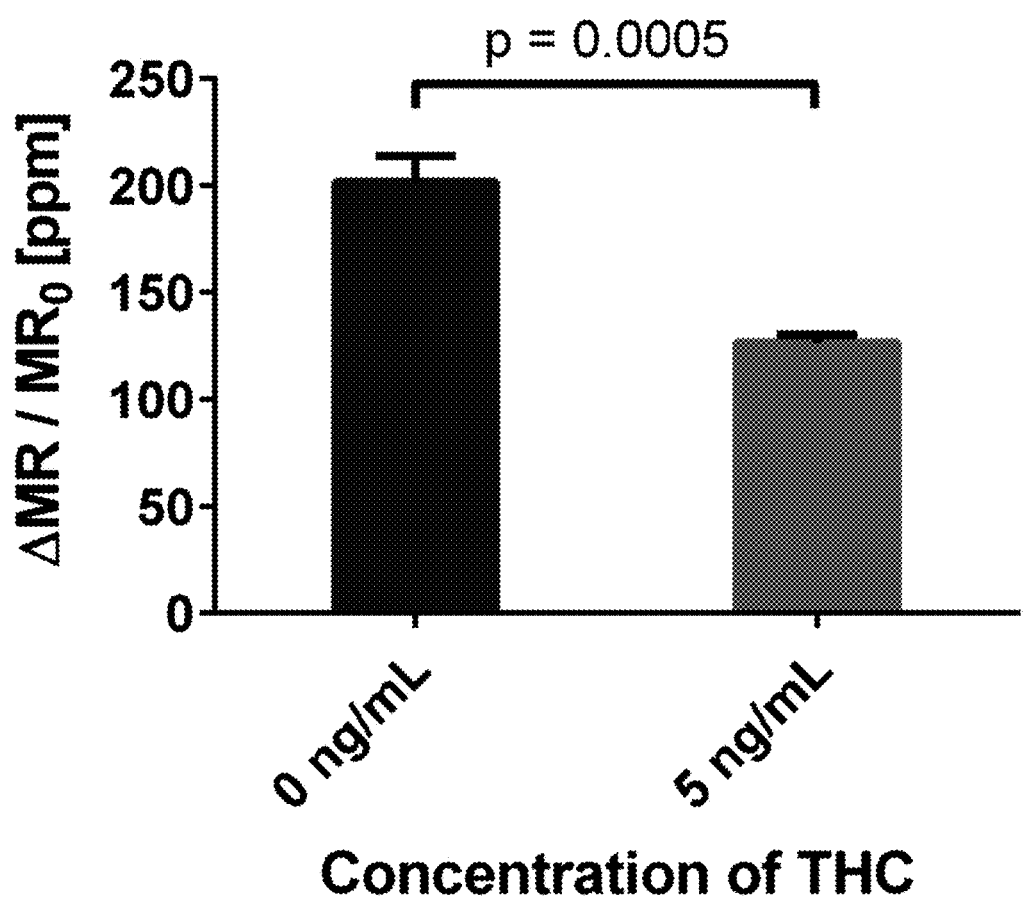
FIG. 4D is a graph of GMR biosensor signal vs analyte (THC) concentration in blood, according to an embodiment of the invention.

In addition, the technique is not limited to saliva, but is capable of detecting small analytes in blood, because GMR biosensors are matrix-insensitive. FIG. 4D shows the measurement of THC spiked in blood. A blood sample was obtained from Stanford Blood Center as blood donation, and either zero or 5 ng/mL of THC was spiked in the blood using a 1:9 mixing ratio. The anti-THC biotinylated antibodies at 50 ng/mL were added to the sample, and the mixture was incubated with the chip. The p-value was determined using Welch's t-test.

Figure 6A:
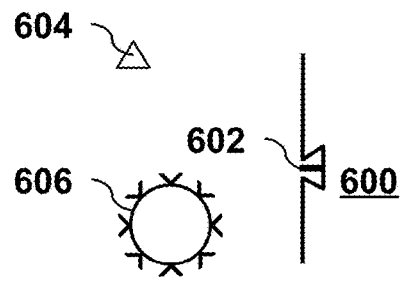
FIGS. 6A-B illustrate a biosensing technique for detection of small molecule analytes in a fluid sample using direct binding in a magnetic biosensor, according to an embodiment of the invention.
Figure 6B:
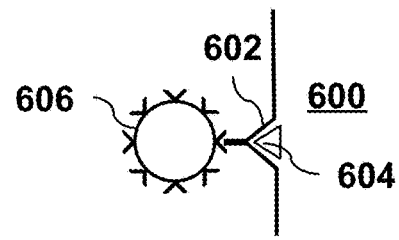

In another aspect, the invention provides a method for detection of small molecule analytes in a fluid sample using direct binding in a magnetic biosensor, as illustrated in FIGS. 6A-B. A magnetic biosensor element 600 is functionalized with a capture probe 602 that changes conformation upon binding to the analytes 604, as shown in FIG. 6A. The conformation changes in the capture probe 602 when bound to the analyte 604 then enable the capture probe to bind to the magnetic tags 606, as shown in FIG. 6B. The process thus includes adding a fluid sample containing the analytes and magnetic tags to the magnetic biosensor functionalized with the capture probes. The binding of the magnetic tags bound to the capture probes of the magnetic biosensor is measured, and the amount of analytes in the solution is determined from the measured binding of the magnetic tags to the capture probes. This technique can also be used with control sensor elements, and may also be adapted for multiplexing using differently functionalized regions of a sensor array.

The invention claimed is:

1. A method for detection of analytes in a fluid sample using competitive assay in a magnetic biosensor, the method comprising:

adding the fluid sample containing the analytes, detection probes, and magnetic tags to the magnetic biosensor, wherein the analytes have weights less than 1000 Daltons;

wherein the magnetic biosensor is functionalized with a capture probe that shares an epitope with the analytes;

wherein the detection probe is capable of binding to the epitope shared by the analytes and the capture probe; and measuring binding of the magnetic tags to the magnetic biosensor via the detection probes and the capture probes, wherein the detection probes are capable of binding to the capture probe, to the analytes, and to the magnetic tags, wherein the analytes and the capture probes compete for binding to the detection probe;

determining an amount of analytes in the solution from the measured binding of the magnetic tags to the magnetic biosensor.

2. The method of claim 1 further comprising
mixing two or more of the fluid sample, detection probes, and magnetic tags together prior to adding them to the magnetic biosensor.

3. The method of claim 1 further comprising
conjugating the detection probes and the magnetic tags prior to their addition to the magnetic biosensor.

4. The method of claim 1 wherein adding the fluid sample, detection probes, and magnetic tags to the magnetic biosensor comprises adding the fluid sample, detection probes, and magnetic tags sequentially to the magnetic biosensor.

5. The method of claim 1 wherein the magnetic biosensor comprises multiple magnetic biosensor elements.

6. The method of claim 5 wherein control biosensor elements of the magnetic biosensor are not functionalized with capture probes that can bind to the analytes or to the detection molecules, and wherein determining the amount of the analytes comprises comparing the measurements of binding of the magnetic tags to the magnetic biosensor with measurements from the control biosensor elements.

7. The method of claim 5 wherein the magnetic biosensor elements are functionalized with different types of capture probes that share corresponding distinct types of epitopes with multiple corresponding distinct types of analytes, wherein the fluid sample contains the multiple distinct types of analytes, and wherein the method further comprises
adding multiple distinct types of detection probes to the magnetic biosensor, wherein the multiple distinct types of detection probes are capable of binding the multiple corresponding distinct types of epitopes.

8. The method of claim 5 further comprising
measuring binding of the magnetic tags to the magnetic biosensor elements functionalized with different types of capture probes;
determining amounts of the distinct types of analytes in the solution from the measured binding of the magnetic tags to the magnetic biosensor elements.

9. The method of claim 1 wherein
determining an amount of analytes in the solution from the measured binding of the magnetic tags to the magnetic biosensor comprises measuring electrical signals from magnetic biosensor elements to detect changes in electromagnetic properties of the biosensor elements due to binding of the magnetic tags.

10. A method for detection of analytes in a fluid sample using competitive assay in a magnetic biosensor, the method comprising:
adding the fluid sample containing the analytes, detection probes, and magnetic tags to the magnetic biosensor, wherein the analytes are THC analytes and have weights less than 1000 Daltons;

wherein the magnetic biosensor is functionalized with a capture probe that shares an epitope with the analytes;

wherein the detection probe is capable of binding to the epitope shared by the analytes and the capture probe; and measuring binding of the magnetic tags to the magnetic biosensor via the detection probes and the capture probes, wherein the detection probes are capable of binding to the capture probe, to the analytes, and to the magnetic tags, wherein the analytes and the capture probes compete for binding to the detection probe;

determining an amount of analytes in the solution from the measured binding of the magnetic tags to the magnetic biosensor.

11. The method of claim 10 further comprising
mixing two or more of the fluid sample, detection probes, and magnetic tags together prior to adding them to the magnetic biosensor.

12. The method of claim 10 further comprising
conjugating the detection probes and the magnetic tags prior to their addition to the magnetic biosensor.

13. The method of claim 10 wherein adding the fluid sample, detection probes, and magnetic tags to the magnetic biosensor comprises adding the fluid sample, detection probes, and magnetic tags sequentially to the magnetic biosensor.

14. The method of claim 10 wherein the magnetic biosensor comprises multiple magnetic biosensor elements.

15. The method of claim 14 wherein control biosensor elements of the magnetic biosensor are not functionalized with capture probes that can bind to the analytes or to the detection molecules, and wherein determining the amount of the analytes comprises comparing the measurements of binding of the magnetic tags to the magnetic biosensor with measurements from the control biosensor elements.

16. The method of claim 10 wherein
determining an amount of analytes in the solution from the measured binding of the magnetic tags to the magnetic biosensor comprises measuring electrical signals from magnetic biosensor elements to detect changes in electromagnetic properties of the biosensor elements due to binding of the magnetic tags.

17. The method of claim 10 wherein the method does not require washing between sample addition and analyte detection to remove background signal and provide required sensitivity.

18. The method of claim 10 wherein the method does not include a washing step that removes magnetic tags from the magnetic sensor arrays.

* * * * *